United States Patent [19]

Davies et al.

[11] Patent Number: 5,008,015

[45] Date of Patent: Apr. 16, 1991

[54] PURIFICATION OF PHOSPHORUS COMPOUNDS

[75] Inventors: Paul M. Davies, Birmingham; Raymond A. Smith, Walsall, both of England

[73] Assignee: Albright & Wilson Limited, Warley, England

[21] Appl. No.: 429,389

[22] Filed: Oct. 31, 1989

[30] Foreign Application Priority Data

Nov. 2, 1988 [GB] United Kingdom ............... 8825589

[51] Int. Cl.$^5$ ............................................. B01D 11/04
[52] U.S. Cl. ..................................... 210/634; 564/15; 562/14
[58] Field of Search .................. 210/634, 906; 564/15; 562/14

[56] References Cited

U.S. PATENT DOCUMENTS 3,288,846 11/1966 Irani et al. ........................ 260/500

FOREIGN PATENT DOCUMENTS

| | | | |
|---|---|---|---|
| 624695 | 5/1963 | Belgium | 562/14 |
| 0125766 | 11/1984 | European Pat. Off. | |
| 213853 | 3/1968 | U.S.S.R. | 562/14 |
| 1276822 | 6/1972 | United Kingdom | |
| 1435878 | 5/1976 | United Kingdom | |
| 1479381 | 7/1977 | United Kingdom | |
| 2021589 | 12/1979 | United Kingdom | |
| 2166741 | 5/1986 | United Kingdom | |

OTHER PUBLICATIONS

Kurt Moedritzer et al., "The Direct Synthesis of α-Amino-methylphosphonic Acids. Mannich-Type Reactions with Orthophosphorous Acid", May 1966, pp. 1603–1607, Research Dept., Inorganic Chemicals Division, Monsanto Company.

Derwent Abstract 15393/E08 (General Chemistry-p. 2, Moscow Lomonosov Univ.-5/15/79, "Purification of Amido or Di:Amido Phosphorous Acids or their Derivitives . . .".

*Primary Examiner*—Stanley Silverman
*Assistant Examiner*—Krisanne Shideler
*Attorney, Agent, or Firm*—Frishauf, Holtz, Goodman & Woodward

[57] ABSTRACT

The content of hydrogen chloride and phosphorous acid of crude amino organic phosphonic acids, especially diethylenetriaminepentakis (methylene phosphonic acid) is reduced by solvent extraction into an alcoholic phase leaving purified phosphonic acid behind.

29 Claims, No Drawings

PURIFICATION OF PHOSPHORUS COMPOUNDS

BACKGROUND OF THE INVENTION

1. Field of the Invention

This invention concerns a purification process, particularly one for separating excess of reactants from aminophosphonates.

2. Background Information

Aminoalkylene phosphonates are used as sequestering agents in for example detergents and may be made by reacting amino compounds, an aldehyde or ketone and phosphorous acid in the presence of hydrochloric acid. The reaction product is an aqueous solution of amino alkylene phosphonic acids with varying degrees of phosphonoalkylation, and excess of carbonyl compound, phosphorous acid and especially hydrogen chloride. As described in U.S. Pat. No. 3288846 and J. Org. Chem. 1966, volume 31, pages 1603–1607, the reaction product in some cases may be worked up by cooling to crystallize out the phosphonate compounds as the free acid. The products are also sold as solutions of their salts e.g. as the sodium salt and in this case the reaction product solution is treated with alkali. But the solution of free acid and salts thereof contain chloride ions which can give rise to corrosion and also in the case of the sodium salt means that the product contains sodium chloride which tends to crystallize out from concentrated salt solution. The chloride content can be reduced by distillation of hydrogen chloride from the free acid but this operation is expensive and may tend to degrade the product, and is corrosive.

SUMMARY OF THE INVENTION

We have discovered that the chloride content can be reduced by solvent extraction.

The present invention provides a process for reducing the chloride content of crude amino organic phosphonic acids, which comprises contacting an aqueous feed comprising amino organic phosphonic acids and hydrogen chloride with liquid organic hydroxylic solvent which is preferably at least partly water immiscible to produce an organic solution containing hydrogen chloride, and usually water, and an aqueous composition comprising the amino organic phosphonic acid of reduced hydrogen chloride content, and separating the composition from the solution.

DETAILED DESCRIPTION OF THE INVENTION

The amino organic phosphonic acid may be of formula I

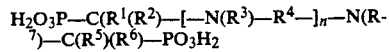

wherein each of $R^1$, $R^2$, $R^5R^6$, which is the same or different, represents a hydrogen atom or an optionally substituted aliphatic hydrocarbyl, alicyclic, aryl or aralkyl group, each preferably of 1–20, especially 1–8, carbon atoms for the aliphatic group or 5–10, 6–18 or 7–19 carbon atoms in respect of alicyclic, aryl or alkaryl groups respectively, and each of $R^3$ and $R^7$, which is the same or different, is as defined for any one of $R^1$, $R^5$ and $R^6$ apart from hydrogen, or is a group of formula

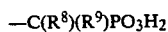

wherein each of $R^8$ and $R^9$, which may be the same or different, is as defined for any of $R^1$, $R^2$, $R^5$ or $R^6$, and $R^4$ represents a divalent organic group e.g. of 1–10 carbon atoms, n is 0 or an integer of at least 1 e.g. 1–5 such as 1 or 2. The aliphatic hydrocarbyl group may be an alkyl or alkenyl group, such as methyl, ethyl, propyl or isopropyl group, butyl, amyl, hexyl, octyl, decyl or dodecyl group. Examples of the optional substituents are one or more alkoxy groups e.g., of 1–8 carbon atoms, hydroxy and halo groups. The alicyclic group may be a cyclopentyl or cyclohexyl group, while the aryl group may be a phenyl or naphthyl group which may optionally be substituted by at least one alkyl, e.g., methyl, halo e.g., chloro or nitro substituent. The aralkyl group may be a benzyl or naphthylmethyl group, optionally substituted by at least one alkyl, e.g., methyl, halo, e.g., chloro or nitro substituent. Preferably $R^1$, $R^5$, and $R^9$ if present, represent hydrogen atoms, and $R^6$ and $R^8$ if present, represent hydrogen atoms or alkyl or aryl, e.g., phenyl or tolyl group.

Most preferably each of $R^1$, $R^2$, $R^5$, $R^6$ and if present $R^8$ and $R^9$, represent hydrogen atoms, while $R^3$ and $R^7$ preferably represent an alkyl or alkoxyalkyl group, e.g., of 4–14 carbon atoms or the group of formula.

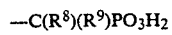

The divalent group of group $R^4$ may be an alkylene group, e.g., of 1–6 carbon atoms such as 1,2-ethylene, 1-3-propylene or 1,4-butylene or other alpha, omega alkylene group, or phenylene, e.g., 1,2- or 1,4-phenylene or cyclohexylene, e.g., 1,1 or 1,4-cyclohexylene. Preferably $R^4$ is an ethylene group.

Thus preferred compounds are nitrilo tris (methylene phosphonic acid), ethylene diamine tetra (methylene phosphonic acid), diethylene triamine penta(methylene phosphonic acid) and triethylene tetramine hexa (methylene phosphonic acid) and n-octyl or 2-ethylhexyl amino bis (methylene phosphonic acids), and hexylene 1,6-diamine tetra (methylene phosphonic acid).

These crude amino organo phosphonic acids, made from the amine, aldehyde or ketone and phosphorous acid, preferably contain a majority of the desired phosphonic acid product, e.g., 50–100% especially 50–80% and usually a minority of amino organo phosphonic acids with less than the optimum proportion of phosphonic acid groups per nitrogen atom; these other compounds can contain N-H groups or N-methyl groups in replacement of one or more but not all of the organophosphonic acid groups.

In this specification, unless otherwise stated, the percentage concentration of amino organo phosphonic acids is expressed on the assumption that all acid species, apart from hydrochloric acid, are amino organo phosphonic acids and that all the latter have organo phosphonate groups replacing every hydrogen atom bonded to a nitrogen atom in the amine of formula

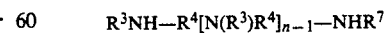

wherein each of $R^3$ and $R^7$ is as defined above or represents hydrogen. The analyses for the acid species can be performed by base titration with compensation made for the hydrochloric acid present. Total analyses for all the P species present may be made by P. N.M.R.

The aqueous feed of amino organic phosphonic acid and hydrogen chloride can contain 10–70%, e.g.,-

40–60% of the amino organic phosphonic acid species in total and 1–15% e.g., 4–15% such as 7–13% of hydrogen chloride in the solution or 2–40%, e.g., 10–40% or 20–35% of hydrogen chloride relative to the weight of amino organic phosphonic acid species; the solution may also contain phosphorous acid, e.g., in amount of 0.1–10% such as 0.1–5% or 1–8%, 0.1–5% of phosphoric acid and 0.1–2% of aldehyde or ketone e.g., formaldehyde. The aqueous solution is usually at pH of less than 2.

The crude aqueous feed of amino organic phosphonic acid may be an aqueous solution or suspension and may be contacted with the solvent directly from the preparation. Alternatively, the aqueous reaction mixture produced directly in the preparation may be cooled first and before contact with solvent any solid which deposits separated first. Usually the crude aqueous phase is a solution not a suspension though the latter may be preferred in the case of ethylene diamine tetra (methylene phosphonic acid).

The aqueous solution is contacted with the organic solvent to extract the hydrogen chloride and usually also the phosphorous acid into an organic solution and to leave a separate aqueous medium. The organic solvent is an hydroxylic compound which is capable of giving this separate aqueous medium and preferably at least partly water immiscible; its solubility in water at 20° C. is usually 0.1–15%, e.g., 0.1–10% especially 0.1–5% or 5–10%, while the solubility of water in the solvent at 20° C. is usually 0.1–25% such as 0.1–8% or 8–20%. Chemically they are usually alkanols of 3–12 carbon atoms e.g., 4–12 or 4–9 carbon atoms such as isopropanol or propanol, n-,iso-, sec or tert butanol, n-amylalcohol, isoamylalcohol, tert. amylalcohol, hexanol, n-octanol and 2-ethylhexanol, decanol, or cyclo alkanols of 4–7 carbons such as cyclohexanol; a butanol or an amyl alcohol is preferred. There may also be used alkoxyalkanols of 3–10 carbon atoms such as monoalkyl ethers of ethylene or propylene glycols, e.g., methyl -, ethyl-,butyl- or hexyl-mono ethers of ethylene glycol. A hydroxylic compound is used which in the relation to the amount of amino organo phosphonic acid solution gives a liquid organic phase and a separate aqueous phase, which may be a solution or suspension; isopropanol is miscible with water but forms 2 liquid phases when mixed in equal volume with the amino organic phosphoric acid solution. While the solvent may be used anhydrous, it usually contains dissolved water in amounts of up to the saturation concentration, e.g., 40–100% thereof or less, especially significantly less, than the saturation concentration e.g., 10–60% thereof.

The aqueous feed and solvent may be mixed in weight ratios of 0.1–10:, e.g., 0.3–3.0:1 such as 0 5–2.0:1. The contact may be in one stage, or more than one stage, e.g., 1–10 stage and may be batch wise or continuous.

The contact may be performed at 0–120° C., subject to non boiling of the solvent, e.g., 10–50° C. but is preferably at 30°–80C. or 50°–110° C., so the contact may be on the hot reaction mixture direct from the preparation. Advantageously the separation of composition and organic solution is also performed at a temperature in these ranges, and particularly within the same temperature ranges.

The contact produces an organic solution containing hydrogen chloride and usually water, which is separated from the aqueous composition comprising the amino organic phosphonic acid. The latter composition may be a suspension of solid, when the organic phase has absorbed at least a significant amount of water and chloride to leave a solid suspension of amino organic phosphonic acid phase, which can then be filtered from the rest of the aqueous phase. In some cases the filtration is difficult and then it is better to heat the suspension to redissolve the solid and/or to have diluted the crude amino organic phosphonic acid with water before contact with solvent. The mixture of organic solution and an aqueous medium which is a suspension of solid amino organic phosphonic acid in a concentrated solution thereof is preferably filtered first to remove the solid and then two the liquid phases are separated. Preferably however the composition comprising the amino organic phosphonic acid is an aqueous solution thereof and the two liquid phases are separated if necessary or desired with heating to keep the contact and separation stages warm to stop any solidification.

In the case where the contact produces two liquid phases, with or without an extra solid phase, the contact is preferably in more than one stage in cross-or countercurrent in discrete mixer settlers or in columns, which may be perforated optionally stirred contactors or pulsed disc contactors. The contact may be in 1–10 stages, especially 2–7 stages, the more stages being used with solvents of highest carbon contents or lowest water solubilities, or for the lowest chloride contents for the product amino organic phosphonic acids.

The contact is preferably such that with the particular solvent and volume ratio of aqueous feed solution to solvent, the organic solution in a one stage contact contains 5–70% of the total hydrogen chloride and over the whole extraction the organic solution contains 60–90% of the total hydrogen chloride.

When the contact produces two liquid phases, or after any solid is removed from the aqueous liquid phase, and the aqueous phase has been separated, the aqueous phase can be worked up as required.

Particularly, if its content of residual solvent is very low, e.g., less than 1% it may be sold as such as the free acid, but when it has a higher solvent content, the latter may be removed by steam stripping, which may also reduce any residual carbonyl compound content. In many cases the product is wanted as the at least partly neutralized salt, and in these cases the aqueous phase may be treated with base first, and if desired steam stripped to remove residual solvent.

The process of the present invention provides the purified amino organic phosphonic acid species (or salt thereof), usually containing 0.02–15% such as 0.1–15%, e.g., 1–5% or 2–11% such as 4–10% chloride ion (based on the dry weight of said acid). The purified amino organic phosphonic acid species or salt thereof is usually made by the process of the invention as an aqueous solution of 20–60%, e.g., 40–60% or 40–55% solids content, and 0.05–8%.e.g., 1–6% such as 2–5% chloride ion and 0–8% organic hydroxylic solvent. This acid has a lower chloride content than may be conveniently made by evaporation of hydrogen chloride and therefore tends to be less corrosive and its sodium salts more soluble and less prone to deposition of solids. The acid and its salts also usually have a lower phosphorous acid content and therefore a lower ionic strength.

The organic solution containing hydrogen chloride is separated from the phase containing amino organic phosphonic acid. The solvent can be recovered from the organic solution by contact with water, which strips the hydrogen chloride and may also remove carbonyl compound, e.g., formaldehyde, as well as phosphorous and any phosphoric acid, to leave an organic solvent for reuse to contact fresh aqueous crude amino organic phosphonic acid feed. Alternatively the stripping may be done with an aqueous solution comprising base, e.g. an alkali such as sodium hydroxide, to produce a solvent layer of lower water content than in the case of water stripping, and an aqueous solution comprising the chloride salt; the wet solvent layer can then be reused for reextraction. If desired the organic solution containing hydrogen chloride and a small amount of amino organic phosphonic acid may be scrubbed with water to reduce the content of the latter and produce a purified organic solution for work up as described above and an aqueous phase containing recovered amino organic phosphonic acid values which can be recycled to the original extraction step.

The invention is illustrated in the following Examples, in which parts are by weight, and analyses for hydrochloric acid are expressed in terms of chloride ion.

EXAMPLE 1

A solution containing diethylene triamine (38.6 part), concentrated hydrochloric acid (152.1 parts) and phosphorous acid (153 parts) was heated to reflux and an aqueous solution of formaldehyde (37%w/w strength, 172 parts) was added dropwise over 10 minutes to give a Product solution of crude diethylene triamine penta(-methylene phosphonic acid) DETMPA which was analysed by phosphorus n.m.r. as containing (by weight of total amino organo phosphonic acid expressed as described above) 67.1% DETMPA, 19.6% of the corresponding N methyl N tetra ( methylenephosphonic acids), small amounts of analoguous compounds with N-H or NN dimethyl groups, hydroxymethyl phosphonic acid, 3.8% phosphorous acid and 1% phosphoric acid and 4.4% others. The solution also contained 10% hydrochloric acid, i.e., weight ratio of chloride ion to amino organo phosphonic acid of 1:3.83. The Product solution was allowed to cool.

66.5 parts of the Product solution was contacted at 45°C. for 30 minutes with 42 parts of butan-1-ol saturated with water (about 20% water content) and stirring. The mixture obtained was cooled to room temperature and allowed to separate to give 49.7 parts of a heavier aqueous phase containing the DETMPA and 45.5 parts of a lighter organic layer containing the chloride. The phases were separated and analyzed. The organic layer contained 0.7% by weight of amino organo phosphonic acids, and also hydrochloric acid in a weight ratio of 1:7. The aqueous layer contained a weight ratio of amino organo phosphonic acid, primarily DETMPA, to hydrochloric acid of 6.95:1. The total amino organo phosphonic acid was analyzed by P N.M.R. as 72.1% of DETMPA, 20.5% of the N methyl compounds, 0.5% of hydroxymethylene phosphonic acid, 1.8% phosphorous acid and 0.4% phosphoric acid.

32.5 parts of the aqueous layer from this extraction were reextracted with 21 parts of fresh wet butanol at room temperature to give 23 parts of an aqueous layer and a second organic layer which were separated. The second aqueous layer contained a weight ratio of amino organo phosphonic acid to hydrochloric acid of 14.4:1; the amino organo phosphonic acid was analyzed by P N.M.R. as containing 71.0% of DETMPA, 21.7% of the N methyl compounds, 0-8% of hydroxymethyl phosphonic acid, 0.8% of phosphorous acid and 0.4% phosphoric acid.

The second aqueous layer was then steam stripped to remove residual solvent to leave an aqueous purified solution of DETMPA. To this solution was added an aqueous solution of sodium hydroxide to give the partially neutralized sodium salts of DETMPA of reduced chloride content.

EXAMPLE 2

The process of Example 1 was repeated with 66.5 parts of the Product solution containing crude DETMPA contacted at room temperature for 20 minutes with 165.1 parts of 2-ethylhexan-1-ol saturated with water at room temperature. Separation for five minutes gave 56.8 parts of a heavier aqueous layer containing the DETMPA and a lighter organic layer which were separated. The organic layer contained 0.015% by weight of amino organo phosphonic acid (including phosphorous acid), and hydrochloric acid in a weight ratio of 1:84. The aqueous layer contained amino organo phosphonic acid, primarily DETMPA (including phosphorous acid), and hydrochloric acid in a weight ratio of 5.86:1.

EXAMPLE 3

The process of Example 1 was repeated with 65.7 parts of the Product solution containing crude DETMPA contacted at room temperature for 20 minutes with 81.5 parts of isoamylalcohol saturated with water at room temperature. Separation for 5 minutes gave 53.6 parts of a heavier aqueous layer containing the DETMPA and a first lighter organic layer which were separated. The organic layer contained 0.21% by weight of amino organo phosphonic acid (including phosphorous acid) and 3.4% hydrochloric acid in a weight ratio of 1:28. The aqueous layer contained amino organo phosphonic acid (including phosphorous acid) and hydrochloric acid in a weight ratio of 8.81:1.

33.3 parts of this aqueous layer were reextracted with a further 20.3 parts of the wet isoamylalcohol at room temperature to give 30.5 parts of aqueous layer containing amino organo phosphonic acid (including phosphorous acid) and hydrochloric acid in a weight ratio of 11.5:1 and a second lighter organic layer which were separated.

21.5 parts of the first organic layer containing 3.4% hydrochloric acid were contacted with 24.8 parts of water to scrub the acid into the aqueous phase and produce 17.9 parts of a stripped organic phase containing only 0.2% hydrochloric acid. The phases were separated. The organic phase could be reused to extract fresh crude DETMPA solution.

EXAMPLE 4

The process of Example 1 was repeated with "wet" isobutanol containing 15% water as the solvent and 2 stage countercurrent contact.

40 parts by weight of the product solution of crude phosphonic acid containing 43% of amino phosphonic acid species (including phosphorous acid) and hydrochloric acid (10.2% chloride ion) was contacted with 53 parts by weight of the wet isobutanol to give 63.2 parts by weight of organic phase containing phosphorous acid and 4.6% chloride ion and 29.8 parts by weight of aqueous purified phosphonic acid containing 51.4% amino phosphonic acid species (including phosphorous acid) and 4.0% chloride ion. The organic phase and aqueous phases were separated.

EXAMPLE 5

100 parts of aqueous crude DETMPA containing 42% amino phosphonic acids, 1.6% phosphorous acid and 9.5% hydrochloric acid was contacted counter-currently 45° C. with a flow of 117 parts of wet butan-1-ol containing 6% $H_2O$ in a 3 stage mixer settler unit, to produce 143 parts of organic phase containing 4.9% hydrogen chloride and about 0.9% amino phosphonic acid species and about 1% phosphorous acid, and 74 parts of an aqueous purified acid containing 54% amino methylene phosphonic acid species 0.3% phosphorous acid and 3.3% hydrochloric acid.

The organic phase was scrubbed with 10 parts of water to produce an organic phase containing a phosphorous acid to amino phosphonic acid species ratio of 10:1 and an aqueous phase containing a phosphorous acid to amino phosphonic acid species weight ratio of 1:3.5. The aqueous phase containing recovered amino phosphonic acid was returned to the extraction to mix with the input crude aqueous DETMPA.

The scrubbed organic phase was washed with aqueous alkali to remove hydrochloric and phosphorous acids into an aqueous phase and reform an organic phase which was recycled to the extraction step as a partially wet solvent.

EXAMPLE 6

The process of Example 1 to produce an amino organic phosphonic acid was repeated using ammonia instead of diethylene triamine as the amine to give a crude phosphonic acid containing 42% by weight nitrilo tris (methylene phosphonic acid) (including phosphorous acid) with 5.9% by weight hydrochloric acid.

400 parts by volume (344 weight parts) of wet butan-1-ol containing 11% by weight of water was contacted counter-currently in a packed column with 220 parts by volume (288.2 weight parts) of the above crude phosphonic acid. After separation of the phases, there was an upper organic phase (470 parts by volume) containing phosphorous acid and 2.7% by weight hydrochloric acid and an aqueous phosphonic acid phase (165 parts by volume) containing 48% by weight nitrilo tris methylene phosphonic acid (including phosphorous acid) with 2.4% by weight hydrochloric acid, a weight ratio of 20:1.

We claim:

1. A process for reducing the chloride content of a crude amino organic phosphonic acid which comprises contacting an aqueous feed comprising an amino organic phosphonic acid and hydrogen chloride with a liquid hydroxylic solvent to produce an organic solution containing hydrogen chloride, and an aqueous composition comprising the amino organic phosphonic acid of reduced hydrogen chloride content, and separating the aqueous composition from the organic solution.

2. The process according to claim 1 wherein the solvent is at least partly water immiscible.

3. The process according to claim 2 wherein the solvent is an alcohol of 4-9 carbon atoms.

4. The process according to claim 3 wherein the alcohol is a butanol or an amyl alcohol.

5. The process according to claim 4, wherein the amino organic phosphonic acid is of a formula $$H_2O_3P\text{---}C(R^1)(R^2)\text{---}[\text{---}N(R^3)\text{---}R^4\text{---}]_n\text{---}N(R^7)\text{---}C(R^5)(R^6)\text{---}PO_3H_2$$

wherein each of $R^1$, $R^2$, $R^5$, $R^6$, which is the same or different, represents a hydrogen atom or a substituted or unsubstituted $C_1$-$C_{20}$ aliphatic hydrocarbyl, $C_5$-$C_8$ alicyclic, $C_6$-$C_{18}$ aryl or $C_7$-$C_{19}$ aralkyl group, and each of $R^3$ and $R^7$, which is the same or different, is as defined above for any one of $R^1$, $R^2$, $R^5$, and $R^6$ apart from hydrogen, or is a group of a formula $$\text{---}C(R^8)(R^9)PO_3H_2$$

wherein each of $R^8$ and $R^9$, which may be the same or different, is as defined above for any of $R^1$, $R^2$, $R^5$, or $R^6$, and $R^4$ represents a divalent organic group of 1-10 carbon atoms and n is zero or an integer of 1 to 5.

6. The process according to claim 5, wherein the aliphatic hydrocarbyl group is selected from the group consisting of methyl, ethyl, propyl, isopropyl, butyl, amyl, hexyl, octyl, decyl or dodecyl, said aliphatic hydrocarbyl group being unsubstituted or substituted by one or more substituents selected from the group consisting of $C_1$-$C_8$-alkoxy, hydroxy and halo; wherein the alicylic group is selected from the group consisting of cyclopentyl and cyclohexyl; wherein the aryl group is selected from the group consisting of phenyl and naphthyl, said aryl being unsubstituted or substituted by a substituent selected from the group consisting of alkyl, halo and nitro; wherein the aralkyl group is selected from the group consisting of benzyl and naphthylmethyl, said aralkyl being unsubstituted or substituted by a substituent selected from the group consisting of alkyl, halo and nitro and wherein $R^4$ is a $C_1$-$C_6$-alkylene group.

7. The process according to claim 5, wherein $R^1$, $R^5$ and $R^9$ represent hydrogen, wherein $R^2$, $R^6$ and $R^8$ represent hydrogen, alkyl or aryl and wherein $R^4$ is ethylene.

8. The process according to claim 5, wherein $R^1$, $R^2$, $R^5$ and $R^6$ are hydrogen and $R^3$ and $R^7$ are a $C_4$-$C_{14}$ alkyl group, $C_4$-$C_{14}$ alkoxyalkyl group or a group of the formula $\text{---}C(R^8)(R^9)PO_3H_2$, wherein $R^8$ and $R^9$ are hydrogen and $R^4$ is 1,2-ethylene, 1,3-propylene, 1,4-butylene, 1,2-phenylene, 1,4-phenylene, 1,1-cyclohexylene or 1,4-cyclohexylene.

9. The process according to claim 2, wherein the solvent has a solubility of 0.1 to 15% at 20° C. in water and the solubility of water in the solvent at 20° C. is 0.1 to 25%.

10. The process according to claim 9, wherein the solvent is selected from the group consisting of isopropanol, propanol, n-butanol, iso-butanol, sec-butanol, tert-butanol, n-amylalcohol, isoamylalcohol, tert-amylalcohol, hexanol, n-octanol, 2-ethylhexanol, decanol, cyclohexanol, monomethyl ethers of ethylene glycol, monoethyl ethers of ethylene glycol, monobutyl ethers of ethylene glycol and monohexyl ethers of ethylene glycol.

11. The process according to claim 10, wherein the aqueous feed and the solvent are in a weight ratio of 0.1 to 10:1 and are contacted in one to ten stages at a temperature of 0 to 120° C.

12. The process according to claim 11, wherein the weight ratio is 0.5 to 2.0:1, and the temperature is 50° to 110° C.

13. The process according to claim 1, wherein the feed which comprises 40-60% by weight of the amino organic phosphonic acid and 1-15% by weight of the hydrogen chloride and which further comprises phosphorous acid contacts the solvent to produce the aqueous composition and an organic solution comprising hydrogen chloride and phosphorous acid.

14. The process according to claim 1 or 13 where the aqueous feed comprises nitrilo tris or diethylenetriaminepentakis.

15. The process according to claim 1 wherein the composition produced is an aqueous solution of amino organic phosphonic acid.

16. The process according to claim 1 wherein the solvent contacting the aqueous feed contains less than its saturation concentration of water.

17. A process according to claim 16 wherein the organic solution is treated with an aqueous solution of a base to liberate a solvent of reduced chloride and water content which is recycled to contact fresh feed, and an aqueous solution containing chloride and phosphite.

18. The process according to claim 1 wherein the aqueous feed and the solvent in a weight ration of 0.3-3:1 are contacted in more than one stage.

19. The process according to claim 1 wherein the aqueous feed contacts the solvent at 30° to 80° C.

20. The process according to claim 1, wherein the amino organic phosphonic acid is ethylene diamine tetra, triethylene tetramine hexa, n-octyl or 2-ethylhexyl amino bis, or hexylene 1,6-diamine tetra.

21. The process according to claim 1, wherein the aqueous feed comprises 10 to 70% by weight of said amino organic phosphonic acid and 4 to 15% of said hydrogen chloride.

22. The process according to claim 21, wherein the feed comprises 7 to 13% of said hydrogen chloride.

23. The process according to claim 1, wherein the amino organic phosphonic acid of reduced hydrogen chloride content contains 0.02 to 15% of chloride ions, based on the dry weight of the acid.

24. The process according to claim 1, wherein the aqueous feed comprises diethylene triamine penta and 10% hydrochloric acid, wherein the weight ratio of chloride ions to amino organo phosphonic acid is 1:3.83 and wherein the solvent comprises butan-l-ol.

25. The process according to claim 1, wherein the crude amino phosphonic acid comprises diethylene triamine penta and wherein the solvent comprises 2-ethylhexan-l-ol.

26. The process according to claim 1, wherein the crude amino phosphonic acid comprises diethylene triamine penta and wherein the solvent comprises isoamylalcohol.

27. The process according to claim 1, wherein the crude amino phosphonic acid comprises diethylene triamine penta and wherein the solvent comprises isobutanol.

28. The process according to claim 1, wherein the aqueous feed comprises nitrilo tris and the solvent comprises butan-l-ol.

29. The process according to claim 1, wherein the feed comprises 40 to 60% by weight of triamine penta or nitrilo tris and 7 to 13% hydrogen chloride, wherein the solvent comprises butan-l-ol, 2-ethylhexan-l-ol, isoamylalcohol or isobutanol and the solvent contains dissolved water in an amount of 10 to 60% of its saturated content of water, wherein the aqueous feed and the solvent are in a weight ratio of 0.5 to 2.0:1 and are contacted in one to ten stages at a temperature of 50° to 110° C. and wherein the amino organic phosphonic acid of reduced hydrogen chloride content contains 0.02 to 15% of chloride ions, based on the dry weight of the acid.

* * * * *